United States Patent [19]
Sridhar

[11] Patent Number: 5,626,733
[45] Date of Patent: May 6, 1997

[54] PROCESS FOR THE PREPARATION OF KETO COMPOUNDS

[75] Inventor: Srinivasan Sridhar, Marl, Germany

[73] Assignee: Huels Aktienegsellschaft, Marl, Germany

[21] Appl. No.: 531,589

[22] Filed: Sep. 22, 1995

[30] Foreign Application Priority Data

Sep. 22, 1994 [DE] Germany .......................... 44 33 823.6

[51] Int. Cl.$^6$ .................................................. B01D 61/44
[52] U.S. Cl. ........................... 204/529; 204/530; 204/537; 204/541
[58] Field of Search .................................. 204/529, 530, 204/537, 541

[56] References Cited

U.S. PATENT DOCUMENTS 4,802,965  2/1989  Puetter et al. .......................... 204/530

FOREIGN PATENT DOCUMENTS 4233191  7/1993  Germany.

OTHER PUBLICATIONS

Patent Abstracts of Japan, vol. 7, No. 201 (C–184), Sep. 6, 1983 and Derwent Abstract AN–83–714792 [29], JP–A–58 099473, Jun. 13, 1983.

Primary Examiner—Arun S. Phasge
Attorney, Agent, or Firm—Oblon, Spivak, McClelland, Maier & Neustadt

[57] ABSTRACT

A process for the preparation of keto compounds from the associated alkali metal salts, in which process protonation is carried out by electrodialysis in a nonaqueous medium without the addition of acid which is foreign to the system, and the keto compounds are thereby liberated.

9 Claims, 1 Drawing Sheet

PROCESS FOR THE PREPARATION OF KETO COMPOUNDS

BACKGROUND OF THE INVENTION

1. Field of the Invention

The present invention relates to a novel process for the preparation of keto compounds from alkali metal salts via electrodialysis.

The keto compounds prepared according to the invention method are valuable intermediates in the preparation of, for example, heterocyclic compounds, pharmaceuticals, plant protection agents and aroma substances.

2. Discussion of the Background

Ester condensation can be used to convert carboxylic esters to dicarbonyl compounds. Using this method, ethyl acetoacetate can be prepared from ethyl acetate. Lactones, too, can be converted using ethyl acetate into the corresponding acetyl derivatives. Because of the relatively low reactivity of the ester carbonyl group, however, strong bases such as alkali metal alcoholates are required as condensing agents. These compounds can be prepared by reacting an alcohol with the alkali metal or with alkalis. The alcoholates can also be prepared in an electric field, for example by the amalgam method or in accordance with DE-A-42 33 191 by electrodialysis.

The ester condensation of lactones with carboxylic esters is one method for the preparation of acyl lactones. Owing to the sensitivity of many lactones the condensing agents preferably used, in accordance with Angew. Chemie 71, 709–752, (1959), are sodium, potassium, Na methylate, Na hydride, Na amide, diisopropylmagnesium bromide and triphenylmethylsodium.

To prepare 2-acetylbutyrolactone from γ-butyrolactone and ethyl acetate, processes have been developed in which sodium, NaH and Na alcoholates (JP 70/009 538) are employed as condensing agents. A further process (JP 83/099 473) requires solvents, such as dimethylformamide, to be used in the reaction of γ-butyrolactone and ethyl acetate with sodium methylate to give 2-acetylbutyrolactone. Acid halides are also mentioned as possible condensing agents (JP 83/162 585).

The following features are characteristic of general ester condensation: the condensing agent must always be employed in at least equimolar quantities (1 mol per mole of β-keto compound). The corresponding consumption of the agent is unavoidable. Furthermore, the initial product is an alkali metal salt of the β-keto compound. Consequently, in principle, a salt precursor is present which must subsequently be converted, in a second step, into the desired free β-keto compound. This is carried out by adding a strong acid to the salt. This step of protonation yields the free β-keto compound and the alkali metal salt of the acid which was added. The individual reaction steps are illustrated below using ethyl acetoacetate as example, with the salt of the keto ester being shown in the enol form:

1. Condensation:

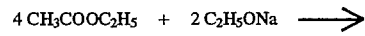

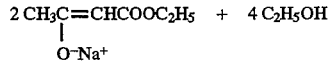

2. Protonation:

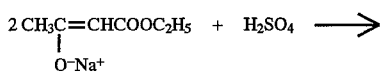

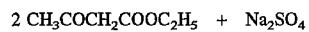

The introduction of the alkali metal ion by the condensing agent leads inevitably to the production of an alkali metal salt after protonation ($Na_2SO_4$ in the above example). Since the quantities involved here are not catalytic but molar, the reactions unavoidably involve the production of relatively large quantities of the salt. Thus, in this reaction a valuable condensing agent is consumed and a worthless salt is produced which, furthermore, has to be disposed of.

OBJECTS OF THE INVENTION

One object of the present invention is to provide a method which overcomes the above-mentioned disadvantages.

This object has been achieved in the present invention by the discovery of a method for the preparation of keto compounds wherein an alkali metal salt intermediate is protonated by electrodialysis in a nonaqueous medium preferably without the addition of acid, particularly acid which is foreign to the system, so as to liberate a keto compound. Suitable alkali meal salts are, preferably, the sodium and potassium salts.

DETAILED DESCRIPTION OF THE INVENTION

Figure 1:
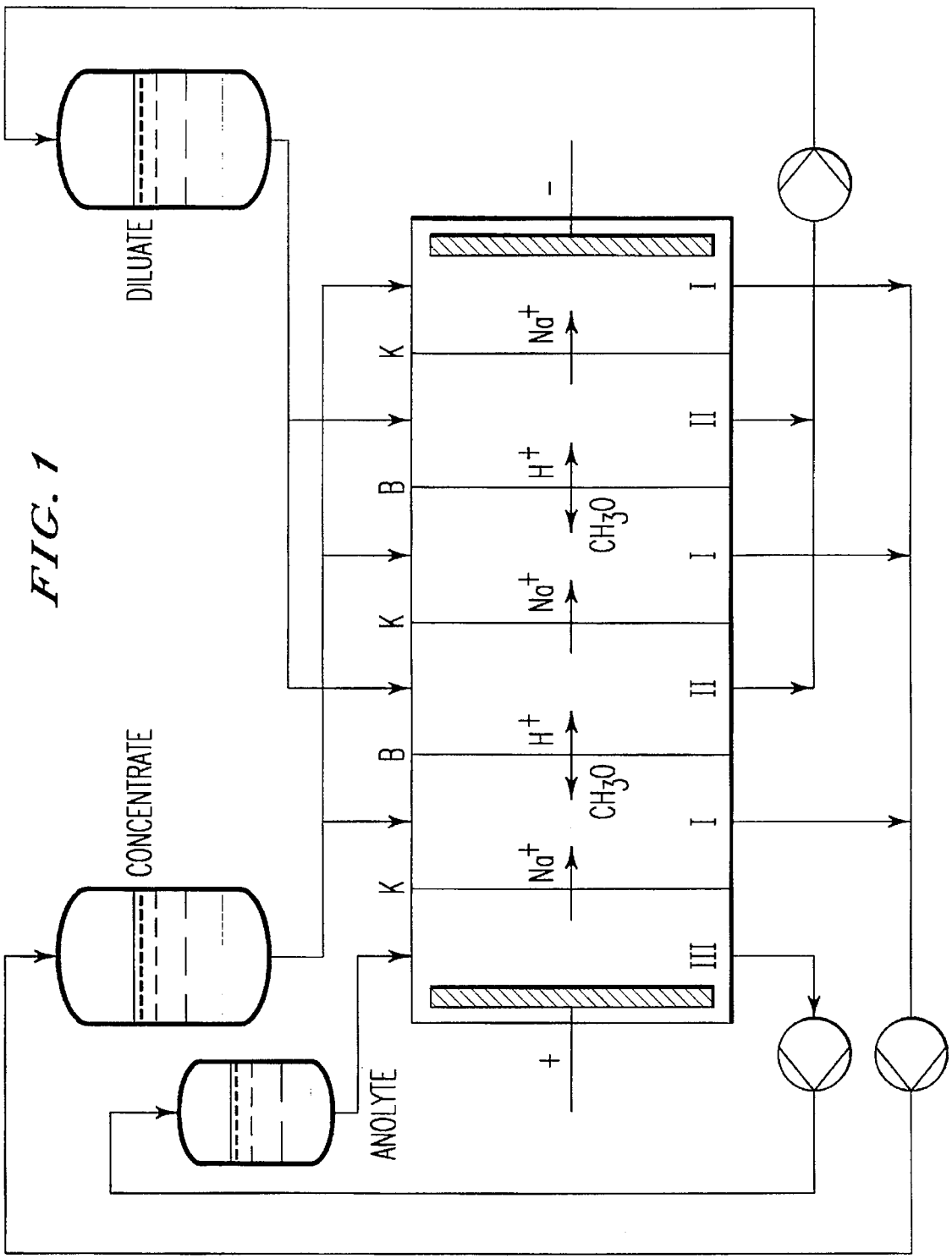
FIGURE 1 shows an electrodialysis cell and describes one embodiment of the invention.

The keto compounds prepared by the invention process may be simple or complex ketones, diketones or keto halides, keto amino acids, keto nitro compounds, etc. They are preferably β-keto esters, and especially β-keto lactones.

Electrodialysis is preferably carried out in an electrodialysis cell having 2 n+2 chambers, where n is a number from 1 to 50. In particularly preferred cases n is a number from 1 to 10 including all numbers and subranges between these several limits.

Suitable nonaqueous media for use in the invention protonation reaction include polar solvents, for example alcohols of 1 to 5 carbon atoms such as methanol, ethanol, isopropanol or tert-butanol, diols such as glycol and butanediol, or triols such as glycerol. It is also possible to use chlorinated hydrocarbons such as methylene chloride and chloroform, ethers such as tetrahydrofuran, and amides such as formamide and dimethylformamide. Solvent mixtures can also be employed. The nonaqueous solvent of the invention may contain up to 5% by volume water. They may also comprise a reaction starting material or product.

The invention nonaqueous medium preferably comprises an alcohol, so that when the keto compounds are obtained an alkali metal alcoholate can be produced as by-product and can be employed for ester condensation reactions.

Whereas protonation in conventional keto compound preparation methods is brought about by introducing an acid which is foreign to the system, such as the sulphuric acid used in the above-described protonation reaction, the present invention avoids the compulsory introduction of an acid and corresponding anion, such as the sulphate ion, which are foreign to the pre-protonation system.

Electrodialysis is preferably carried out in the present invention at from −20° to +90° C. Within this range, further preference is given to temperatures from 10° to 50° C. All temperature values and sub-ranges between these several limits are included herein.

The invention process has the further advantage that no environmentally polluting salt, requiring removal from the system, is formed. Instead it is possible to get back a condensing agent for ester condensation.

The procedure according to the invention will now be illustrated using as an example an electrodialysis cell comprising 6 chambers, as shown in FIGURE 1: each of the chambers is separated from the others by a cation exchange membrane K and/or a bipolar membrane B. Instead of a single bipolar membrane it is also possible to use a pair of membranes consisting of one anion exchange membrane and one cation exchange membrane. In this case the anion exchange membrane is preferably used facing the anode and the cation exchange membrane facing the cathode. The membranes can be commercially available membranes, provided they are stable in the chosen system. Examples of useful cation exchange membranes are CM1 and C 66-10 F from Tokuyama Corp.

A solution comprising an alcohol is passed into the chambers I. This solution is termed "concentrate". The chambers I are separated on the anode side by cation exchange membranes and on the cathode side by bipolar membranes. The cathode chamber (i.e., the chamber containing the cathode), which is separated from its adjacent chamber by a cation exchange membrane, likewise has "concentrate" passed through it. This is where the inward migration of alkali metal ions from the adjacent chambers II and/or from the anode chamber III results in the production of the alkali metal alcoholate.

Pumped through the adjacent chambers II, which are separated by bipolar membranes (on the anode side) and by cation exchange membranes (on the cathode side), is an alcoholic salt solution of a keto compound. This solution is termed "diluate". When an electric field is applied across the chambers the alkali metal ions migrate from the chambers II through the cation exchange membranes K in the direction of the cathode, and enter the chambers I where they form the alcoholate. The bipolar membranes B are traversed by protons. Consequently, in the chambers II, the salt is protonated, producing the free keto compound. A pair of chambers comprising chambers I and II constitutes a functional cell. The feed of the two solutions, the "concentrate" and the "diluate", into the appropriate chambers is preferably carried out in parallel.

The cathode chamber can be supplied with its own alcoholate solution. It can also be used, in accordance with FIGURE 1, as a "concentrate" chamber, since here too the alkali metal ions enter through the cationic exchange membrane. An anolyte may be placed beforehand in the anode chamber III which is possibly an alcoholic solution of sodium acetate. Alternatively, the "diluate" itself can be introduced here (i.e., the anode chamber) as a cation source (not implemented in FIGURE 1), preferably when there is no risk of unwanted reactions at the anode. The electrodialysis can be carried out batchwise or continuously.

In a preferred embodiment of the process according to the invention a β-keto ester is obtained from the salt form thereof while simultaneously carrying out a transesterification. This is a possibility when the alcohol of the "concentrate" is different from the alcohol of the "diluate". Thus, for example, the Na salt of ethyl acetoacetate can be used to obtain the free methyl acetoacetate using methanol.

The possible uses of the process according to the invention are quite diverse and are not limited to keto compounds. The process extends favorably to any reaction in which a reagent is consumed and for which the invention enables the recovery, provision and reuse of this reagent for the reaction. Preferred reactions include the protonation of metal salts to produce an intermediate or final product. Not only alkali metal alcoholates but other valuable compounds can be recovered.

The invention method is preferably used for the Claisen condensation of simple esters and the Dieckmann condensation of diesters, leading to the production of cyclic keto esters and, after hydrolysis and decarboxylation, to cyclic ketones such as, for example, chromanone, coumaranone, cyclohexanedione, hydrindone, piperidone, thiopyranone or indoxylic acid (a capped ketocarboxylic acid). The Dieckmann condensation is also employed for cyclization reactions in steroid synthesis and for cyclizing rearrangements of heterocyclic compounds. The process according to the invention is also suitable for the alcoholate-catalyzed reaction of malonic diester with formamide to give 2,6-dihydroxypyrimidine (a masked ketone).

As mentioned above, in addition to these reactions the process of the present invention can also be applied to other reactions, particularly to those for the preparation of keto compounds. Thus the transacylation of β-keto esters (i.e., the introduction of a new acyl group via an acid halide) which requires an alcoholic alcoholate solution as reagent can be recovered by the method of the invention.

EXAMPLES

In the examples given below for further, non-limiting illustration of the invention, use is made, in accordance with FIGURE 1, of an electrodialysis cell having 6 chambers. The membranes each have a surface area of 100 cm$^2$. The solutions are pumped out of the supply vessels into the chambers and back into the vessels. The "diluate" forms one circuit. The "concentrate" and the catholyte together form a second circuit. The anode is similarly provided with a further circuit. The electrodes used comprise an anode of platinum-coated titanium and a steel cathode. The membranes employed are as follows:

Cation exchange membranes (type C66-10F from Tokuyama Soda, Japan)

Bipolar membranes from the Fraunhofer-Institut für Grenzflächen- und Bioverfahrenstechnik, Stuttgart (a pair of membranes consisting of a membrane out of polysulfone with quaternary ammonium groups and a membrane out of sulfonated polyetheretherketons)

For electrodialysis a voltage of 40 V is applied. The flow rates in each of the circuits are 11 1/h.

Analytical Details

In the following examples sodium methylate formed in the concentrate is determined potentiometrically after appropriate calibration. Sodium determination is carried out by elemental analysis. After each experiment methanol is removed from the diluate in a rotary evaporator under a slight vacuum and the resultant material is then worked up by distillation at 1 hPa via a Claisen stillhead. The gas-chromatographic analyses of the fractions are used to determine the keto compound which is present in free form.

EXAMPLE 1

The initial diluate charge comprises 1,586 g of a 1.66% strength by weight solution of Na acetylbutyrolactone in methanol. The concentrate and the catholyte consist initially of 1,695 g of a solution of 1.23% by weight of sodium methylate in methanol. In the anode chamber, 1,654 g of a 12% strength by weight solution of sodium acetate in methanol are placed as initial charge. Electrodialysis is carried out at 23° C. and terminated after 22 hours.

11.65 g of free acetylbutyrolactone are obtained in the diluate circuit and 50.62 g of sodium methylate in the concentrate circuit.

EXAMPLE 2

The experiment is according to that in Example 1 but lasts for 23 hours using initial quantities of 1,686 g of diluate and 1,516 g of concentrate, with replacement of the sodium acetate anolyte solution by a further 1,456 g of diluate in the anode chamber.

14.1 g of free acetylbutyrolactone are produced in the diluate circuit and 27.85 g of sodium methylate in the concentrate circuit.

EXAMPLE 3

Using initial quantities of 1,688 g of diluate, 1,528 g of concentrate and 1,428 g of anolyte, the procedure of Example 1 is repeated. However, the electrodialysis is carried out at 12° C. and terminated after 51 hours.

22.65 g of free acetylbutyrolactone are produced in the diluate circuit and 68.41 g of sodium methylate in the concentrate circuit.

EXAMPLE 4

As in Example 1 with the following changes: the initial diluate charge comprises 1,268 g of a 7% strength by weight solution of Na ethyl acetoacetate in methanol. The concentrate and the catholyte consist initially of 1,260 g of a solution of 1.25% by weight of sodium methylate in methanol. In the anode chamber, 1,400 g of a 12% strength by weight solution of sodium acetate in methanol are placed as initial charge. Electrodialysis is carried out at 22° C. and terminated after 28 hours.

37 g of free methyl acetoacetate as well as 1.5 g of ethyl acetoacetate are obtained in the diluate circuit and 62 g of sodium methylate in the concentrate circuit.

Accordingly, in this case the transesterification under electrodialysis conditions is already 97% complete after 28 hours.

COMPARISON EXAMPLE A

For transesterification under neutral conditions, two identical mixtures of 47.2 g of free ethyl acetoacetate and 47.2 g of methanol are stirred in a flask at 22° C. for 70 hours. In the case of one mixture, 20 cm² each of the bipolar membrane and of the cation exchange membrane, which membranes were used in the above experiments, are immersed in the flask. 14 g of methyl acetoacetate are ultimately produced in each case, corresponding to a conversion of only 30%.

EXAMPLE 6

As in Example 1 with the following changes: the initial diluate charge comprises 1,257 g of a 9.8 % strength by weight solution of Na methyl acetoacetate in methanol. The concentrate is separated from the catholyte. Each solution forms an independent circuit. The concentrate consists initially of 1,228 g of a solution of 1.26 % by weight of sodium methylate in methanol. The separate, initial catholyte charge comprises 1,211 g of the same solution. In the anode chamber, 1,307 g of an 11.6 % strength by weight solution of sodium acetate in methanol are placed as initial charge. Electrodialysis is carried out at 23° C. and terminated after 24 hours.

66 g of free methyl acetoacetate are produced. In the catholyte circuit 48 g and in the concentrate circuit 47 g of sodium methylate are produced.

This application is based on German patent application P 44 33 823.6 filed Sep. 22, 1994, incorporated herein by reference.

What is claimed as new and is desired to be secured by Letters Patent of the United States is:

1. A process for the preparation of keto compounds from alkali metal salts thereof, comprising the step of protonation of said alkali metal salts by electrodialysis in a nonaqueous medium without the addition of acid and removing the alkali metal ion to form the keto compound.

2. The process according to claim 1, wherein protonation is carried out in an electrodialysis cell having 2 n+2 chambers, where n is a number from 1 to 50.

3. The process according to claim 2, wherein n is a number from 1 to 10.

4. The process according to claim 1, wherein said keto compounds are β-keto esters.

5. The process according to claim 4, wherein said keto compounds are β-keto lactones.

6. The process according to claim 4, wherein a transesterification is carried out simultaneously with protonation by electrodialysis.

7. The process according to claim 1, wherein an alkali metal alcoholate is produced as by-product of said protonation.

8. The process according to claim 1, wherein the protonation is effected at from −20° to +90° C.

9. The process according to claim 1, wherein the protonation is effected at from 10° to 50° C.

* * * * *